Aug. 12, 1941. J. GAUJARD Plant Pat. 482
ROSE PLANT
Filed April 2, 1941
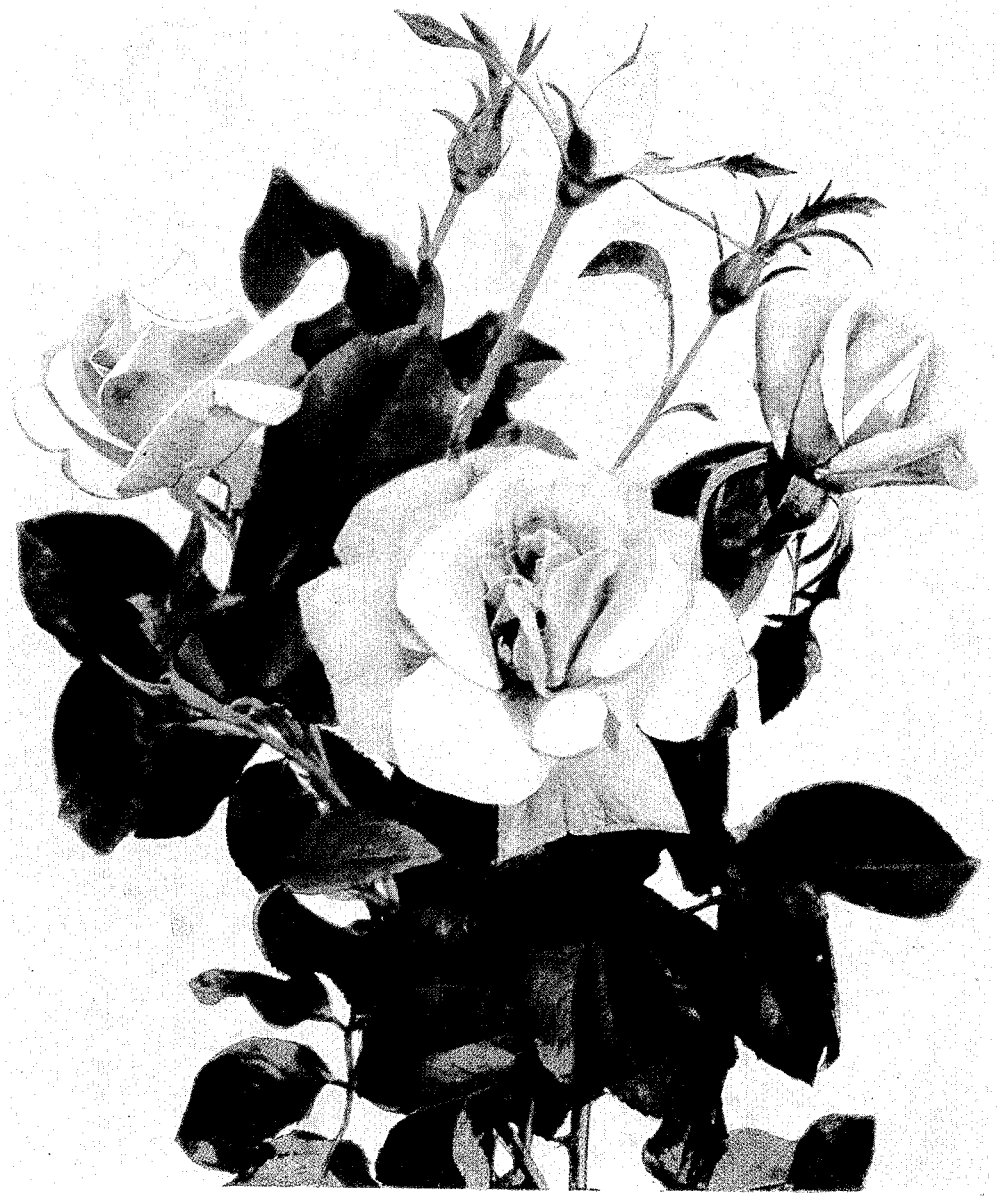
Inventor
Jean Gaujard
By Robb & Robb
Attorneys Patented Aug. 12, 1941

UNITED STATES PATENT OFFICE

482

ROSE PLANT

Jean Gaujard, Feyzin, France, assignor to Jackson & Perkins Company, Newark, N. Y.

Application April 2, 1941, Serial No. 386,523

1 Claim. (Cl. 47—61)

The present invention relates to a new and distinct variety of rose plant, the result of a definite effort to produce an origination distinguishing from either of its parents while combining improvements over both in respect to certain features.

The new variety, illustrated in the different stages of development of the flowers, is a distinctive yellow rose, of light Cadmium color specifically speaking, possesses the important characteristic that the basic yellow of all stages is non-fading.

Structurally, the form of the flowers is irregular with split center when opening, and its petals are thick and satiny which, in the setting of abundant Dark Cress Green and shiny foliage and Garnet Brown new wood presents a very attractive showing which is retained throughout the entire summer.

The following is a detail description of the new variety, the color designations being in accord with Ridgway's Color Standard.

Parentage: Seedling.

*Seed parent.*—Julien Potin.

*Pollen parent.*—Unknown seedling.

Classification: Botanic and commercial—hybrid tea.

*Flower*

Blooming habit: (Observations made in the afternoon of October 1, 1940, at Newark, New York.)

*Recurrent.*—continuous.

Bud:

*Size.*—Medium.

*Form.*—Pointed-ovoid. Is not affected by wet or hot weather.

*Color.*—When sepals first divide—Wax Yellow, Plate 16. When petals begin to unfurl—Apricot Yellow, Pate 4. Edges flushed with Mikado Orange, Plate 3. When half blown:—inside of petals—between Light Cadmium, Plate 4, and Lemon Chrome, Plate 4; reverse of petals—Apricot Yellow, Plate 4.

*Sepals.*—Branched, "hood" above bud. Curl back when bud is half open. *Color:* outside and inside—Bice Green, Plate 17.

*Calyx.*—*Shape*—apple. *Size*—broad. *Aspect*—smooth. *Color*—Bice Green, Plate 17. *Odor when rubbed*—crushed foliage of Harrison's Yellow Rose.

*Peduncle.*—*Length*—medium. *Aspect*—prickly. *Color*—Light Cress Green, Plate 31. *Strength*—erect, heavy.

*Opening.*—Bud opens well. Is not affected by adverse conditions.

Bloom:

*Size.*—Large. Average size when fully expanded—4½ to 5 inches.

*Borne.*—Several together.

*Stems.*—Long; strong.

*Form.*—When first open, high center. *Permanence*—retains its form to the end, opening gradually.

*Petalage.*—Double (full but open center). Number of petals under normal conditions —30.

*Color.*—Center of flower, base of petal—Lemon Chrome, Plate 4, lightening to Empire Yellow, Plate 4, at top of petal. Outer petals—Empire Yellow, Plate 4. Base of petals (aiglet)—Lemon Chrome, Plate 4. Inside of petals, base of petal—Lemon Chrome, Plate 4, lightening to Empire Yellow, Plate 4, at top of petal. Reverse of petals—Empire Yellow, Plate 4, lightening to Pinard Yellow, Plate 4, at base. *General tonality from a distance.*—Light Cadmium, Plate 4.

*Discoloration.*—General tonality at end of first day—Light Cadmium, Plate 4. Second day—Apricot Yellow, Plate 4. Third day—Apricot Yellow, Plate 4.

Petals:

*Texture.*—Thick. Is not affected by wet or hot weather.

*Appearance.*—Inside—satiny. Outside—shiny.

*Form.*—Oval.

*Arrangement.*—Irregular with split center. Petaloids in center—large and small.

*Persistence.*—Drop off cleanly.

*Fragrance.*—Slight. *Nature*—slight tea (average hybrid tea scent). *Lasting quality.* —On the plant and as cut flower—very long.

Genital organs:

*Stamens, anthers:*

*Size.*—Small; many.

*Color.*—Deep Chrome, Plate 3.

*Arrangement.*—Regular around styles.

*Stamens, filaments (threads).*—Long. *Color*—Cadmium Orange, Plate 3.

*Pollen.*—Aniline Yellow, Plate 4.

*Styles.*—Bunched, even; medium length; thin.

*Stigmas.*—Buff Yellow, Plate 4.

*Ovaries.*—Some protruding from calyx.

*Plant*

Form:—Bush.
Growth: Vigorous, upright.
Foliage: 5–7 leaflets.
*Size.*—Medium.
*Quantity.*—Normal.
*Color.*—*New foliage:*—upper side—Madder Brown, Plate 13; under side—Van Dyke Red, Plate 13; center, veining—Oil Green, Plate 5. *Old foliage:*—*upper side*—Dark Cress Green, Plate 31; under side—Light Cress Green, Plate 31.
*Shape.*—Oval pointed.
*Texture.*—Upper side—leathery. *Ribs and veins.*—ordinary.
*Edge.*—Serrated (saw toothed).
*Serration.*—Single; small.
*Rachis.*—Light Elm Green, Plate 17. Under side—rough.
*Stipules.*—Long; bearded.
*Disease resistance.*—Resistant.
Wood:
*New Wood.*—*Color*—Garnet Brown, Plate 1. *Bark*—smooth.
*Old wood.*—*Color*—Cress Green, Plate 31. *Bark*—smooth.
Thorns (thorns are divided into thorns, prickles, and short needles):
*Thorns.*—*Quantity:*—on main stalks from base—many; on laterals from stalk—ordinary.
*Form.*—Broad base, hooked downward.
*Color when young.*—Madder Brown, Plate 13.
*Position.*—Irregular.
*Prickles.*—On main stalks and on laterals—few. *Color*—Madder Brown, Plate 13.

I claim:

A new and distinct variety of rose plant, characterized as to novelty by the distinctive unfading yellow color and irregular form of its flowers, having thick, satiny petals, its shiny green foliage persisting throughout the summer season, and the Garnet Brown of its new wood, substantially as shown and described.

JEAN GAUJARD.